United States Patent
Tahara et al.

(10) Patent No.: US 10,738,360 B2
(45) Date of Patent: Aug. 11, 2020

(54) METHOD FOR ASSISTING DETECTION OF ALZHEIMER'S DISEASE OR MILD COGNITIVE IMPAIRMENT

(71) Applicant: HIROSHIMA UNIVERSITY, Higashihiroshima-shi, Hiroshima (JP)

(72) Inventors: Hidetoshi Tahara, Hiroshima (JP); Masayasu Matsumoto, Hiroshima (JP); Yu Ninose, Hiroshima (JP)

(73) Assignee: HIROSHIMA UNIVERSITY, Higashihiroshima-Shi (JP)

( * ) Notice: Subject to any disclaimer, the term of this patent is extended or adjusted under 35 U.S.C. 154(b) by 0 days.

(21) Appl. No.: 15/557,752

(22) PCT Filed: Mar. 11, 2016

(86) PCT No.: PCT/JP2016/057827
§ 371 (c)(1),
(2) Date: Sep. 12, 2017

(87) PCT Pub. No.: WO2016/148073
PCT Pub. Date: Sep. 22, 2016

(65) Prior Publication Data
US 2018/0067132 A1     Mar. 8, 2018

(30) Foreign Application Priority Data
Mar. 13, 2015   (JP) .................................. 2015-051327

(51) Int. Cl.
*C12Q 1/68* (2018.01)
*C12Q 1/6883* (2018.01)
*G01N 33/50* (2006.01)

(52) U.S. Cl.
CPC ............. *C12Q 1/6883* (2013.01); *C12Q 1/68* (2013.01); *G01N 33/50* (2013.01); *C12Q 2600/158* (2013.01); *C12Q 2600/178* (2013.01)

(58) Field of Classification Search
None
See application file for complete search history.

(56) References Cited

FOREIGN PATENT DOCUMENTS

| EP | 2733219 A1 | 5/2014 |
|----|------------|--------|
| JP | 2014-132863 A | 7/2014 |
| JP | 2015-223165 A | 12/2015 |
| WO | WO 2013/003350 A2 | 1/2013 |
| WO | WO 2015/133477 A1 | 9/2015 |

OTHER PUBLICATIONS

Javed et al BioMed Research Int. Indawi Publishing Corp. 2014. p. 1-19.*
Carreras-Badosa et al. J Clin Endocrinol Metab. Sep. 25, 2015. 100: E1446-E1456.*
Strycharz et al Nutrients. Nov. 15, 2018.10: 1774.*
MacLellan et al BMC Clinical Pathology. published online Jun. 21, 2014. 14:27.*
Blondal et al Methods. 2013 59: S1-S6.*
International Search Report for International Application No. PCT/JP2016/057827, dated Jun. 7, 2016, with English translation.
Kumar et al., "Circulating miRNA Biomarkers for Alzheimer's Disease," Plos One, vol. 8, No. 7, e69807, Jul. 2013, pp. 1-10.
Leidinger et al., "A Blood Based 12-miRNA Signature of Alzheimer Disease Patients," Genome Biology, vol. 14, No. R78, 2013, pp. 1-16.
Müller et al., "MicroRNAs in Alzheimer's Disease: Differential Expression in Hippocampus and Cell-Free Cerebrospinal Fluid," Neurobiology of Aging, vol. 35, 2014 (published on web Aug. 17, 2013), pp. 152-158.
Ninose et al., "Analysis and Use of MicroRNAs in Plasma from Patients with Alzheimer's Disease for its Diagnosis," Annual Meeting of the Molecular Biology Society of Japan Program—Yoshishu, vol. 37, 2F-0947, 2014, 4 pages with an English translation.
Rotllan et al., "MicroRNA Regulation of Cholesterol Metabolism," Cholesterol, vol. 2012, Article ID 847849, 2012, pp. 1-8.
Tahara, "Use of Tests for Telomere Length and MircoRNA in Health Management," Annual Meeting of Japanese Society of Pharmaceutical Health Care and Sciences Koen Yoshishu, vol. 24, 2014, p. 131 with an English translation (3 pages total).
Wang et al., "The Expression of MicroRNA miR-107 Decreases Early in Alzheimer's Disease and May Accelerate Disease Progression through Regulation of β-Site Amyloid Precursor Protein-Cleaving Enzyme 1," The Journal of Neuroscience, vol. 28, No. 5, Jan. 30, 2008, pp. 1213-1223.

* cited by examiner

*Primary Examiner* — Carla J Myers
(74) *Attorney, Agent, or Firm* — Birch, Stewart, Kolasch & Birch, LLP

(57) ABSTRACT

Disclosed is a method for assisting the detection of Alzheimer's disease or mild cognitive impairment, the method for assisting the highly accurate detection of Alzheimer's disease or mild cognitive impairment. In the method for assisting the detection of Alzheimer's disease or mild cognitive impairment, the amount of at least one miRNA selected from miR-122, miR-144, let-7f, miR-128-3p and miR-107 contained in a test sample separated from a living body is used as an indicator. A larger amount of miR-122 than that in a healthy individual, or a smaller amount of at least one miRNA selected from miR-144, let-7f, miR-128-3p and miR-107 than that in a healthy individual is indicative that the living body is more likely to have developed Alzheimer's disease or mild cognitive impairment.

3 Claims, 22 Drawing Sheets
Specification includes a Sequence Listing.

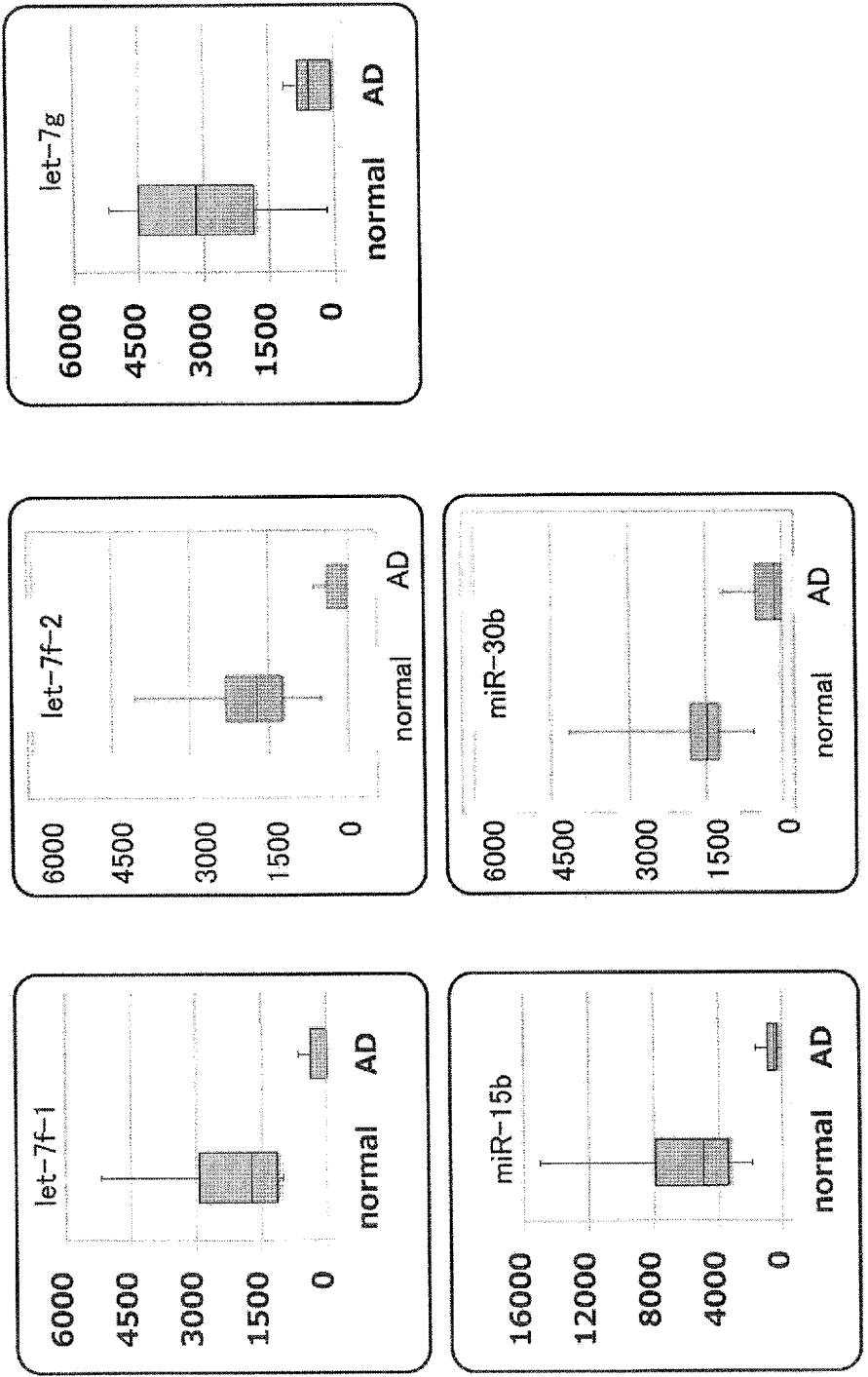
Box plots of expression level of miRNAs each showing a difference between healthy individuals and Alzheimer's patients
* vertical axis: the number of read counts for a miRNA per 1,000,000 reads
Fig.1-A

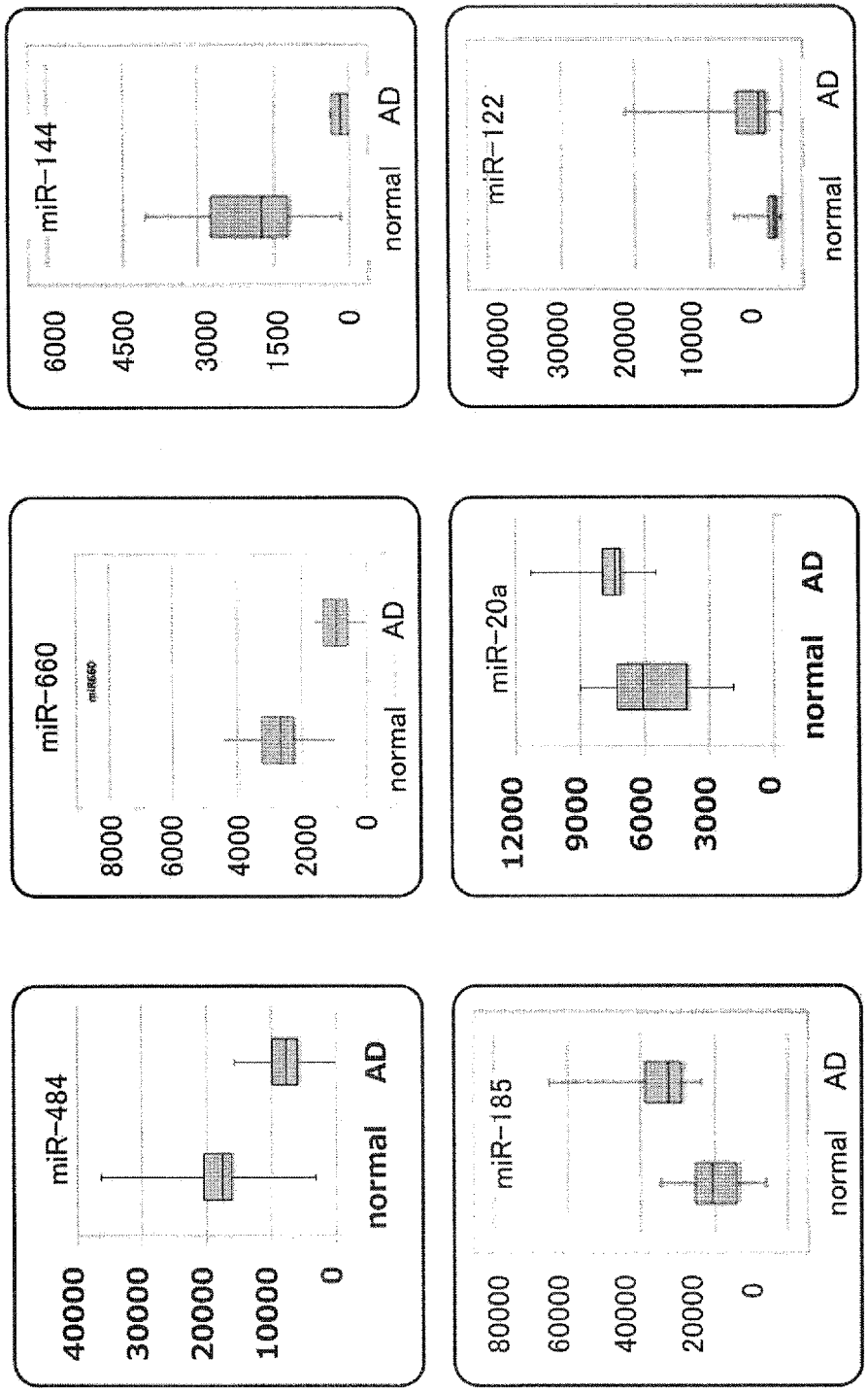
Box plots of expression level of miRNAs each showing a difference between healthy individuals and Alzheimer's patients
* vertical axis: the number of read counts for a miRNA per 1,000,000 reads
Fig.1-B

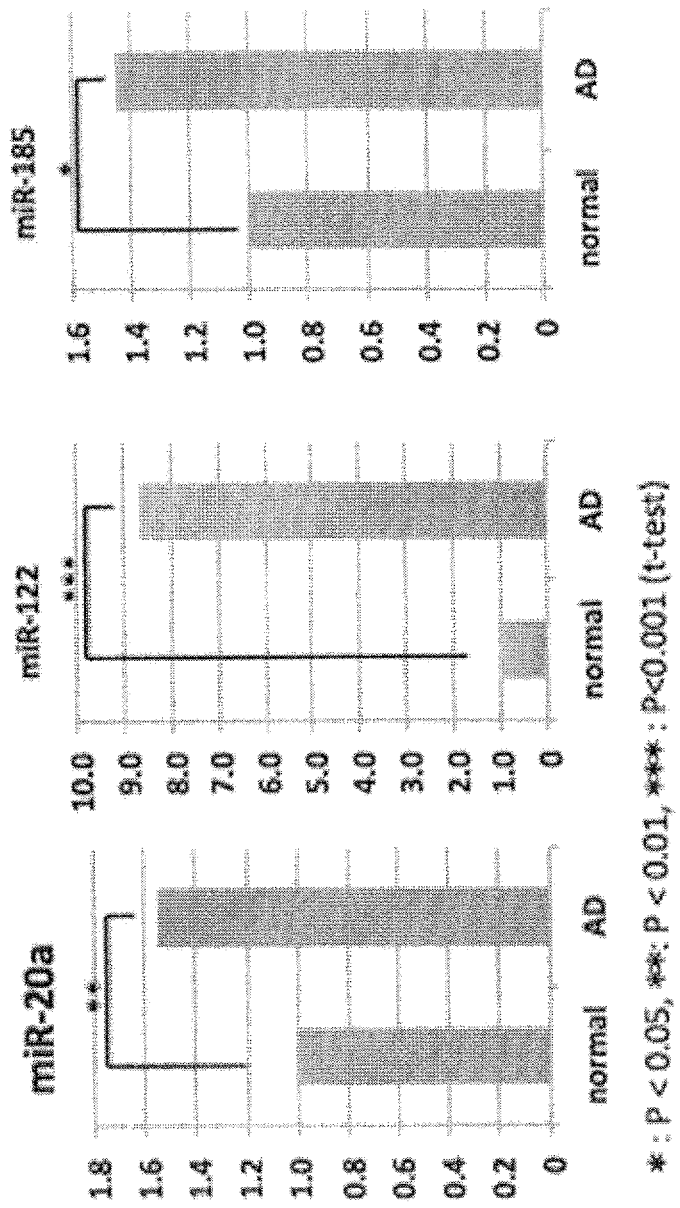
Fig.2-A

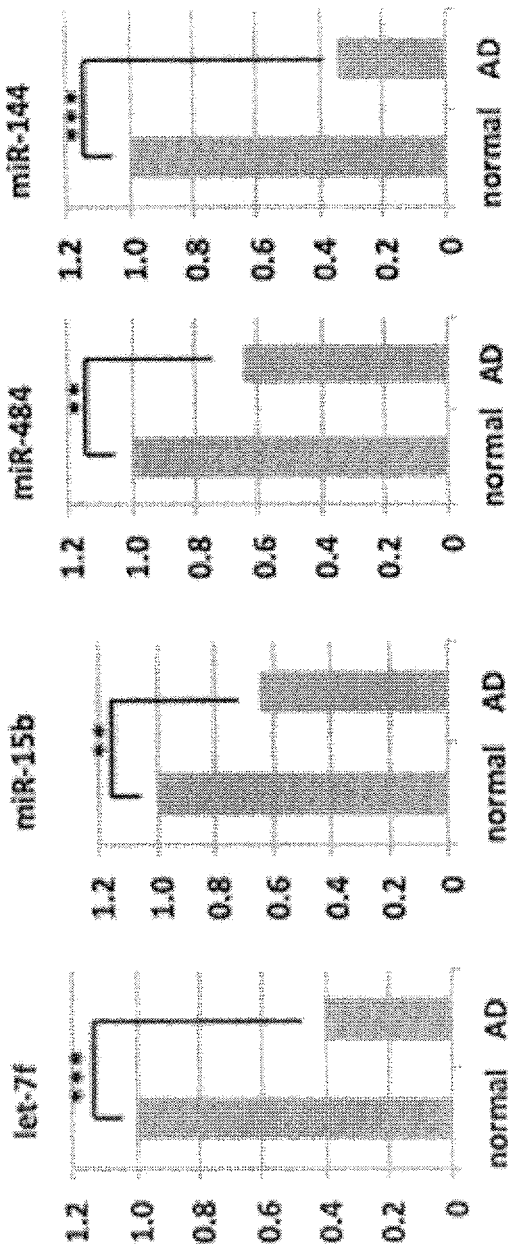
Fig.2-B

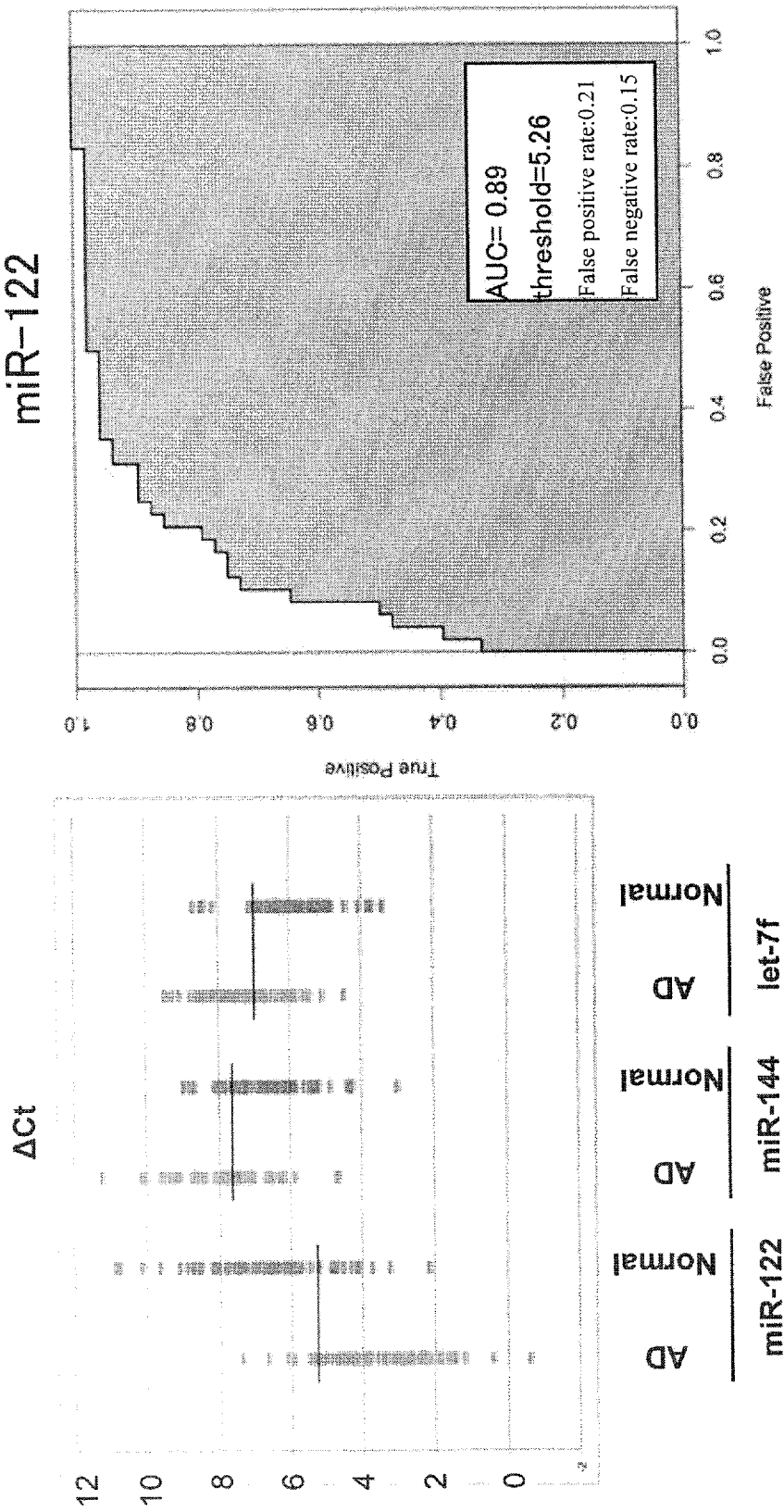
Fig.3-A

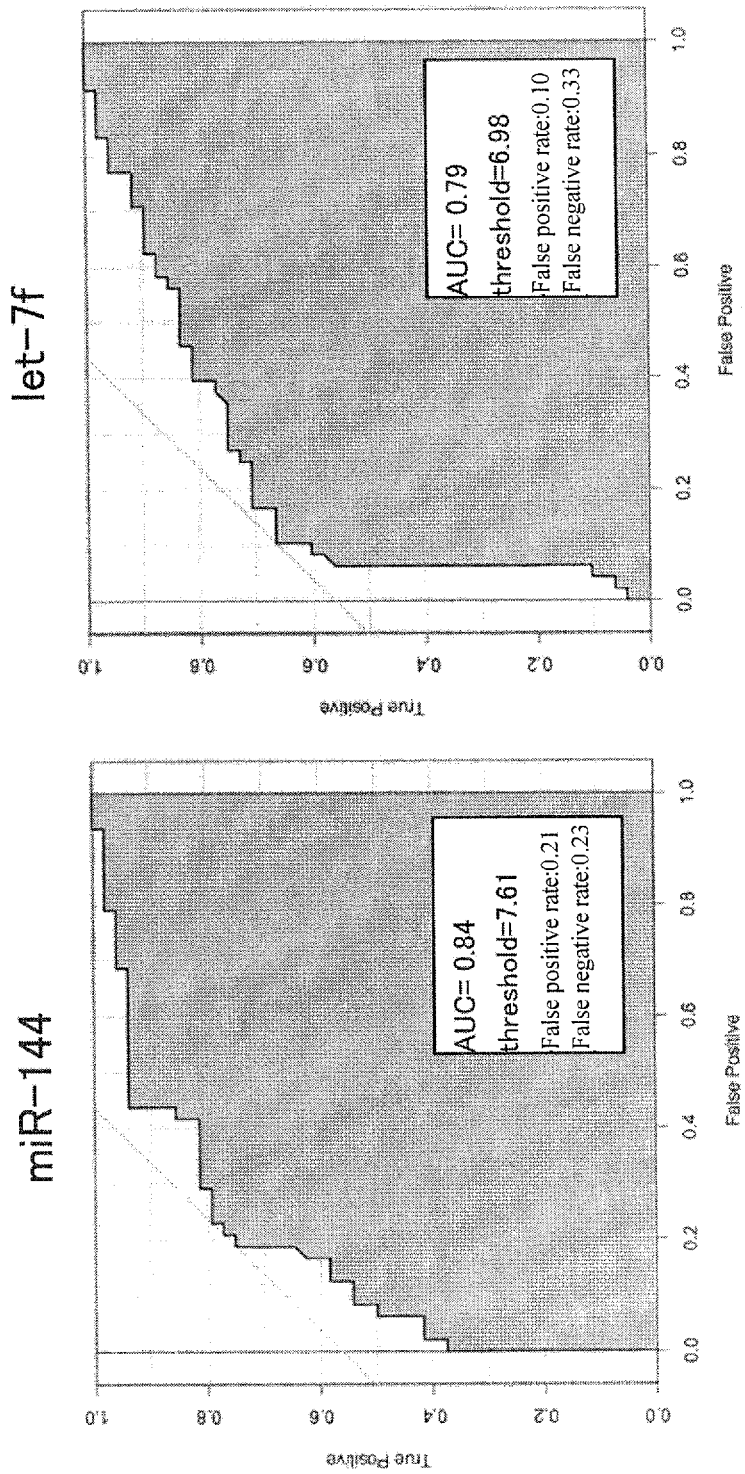
Fig.3-B

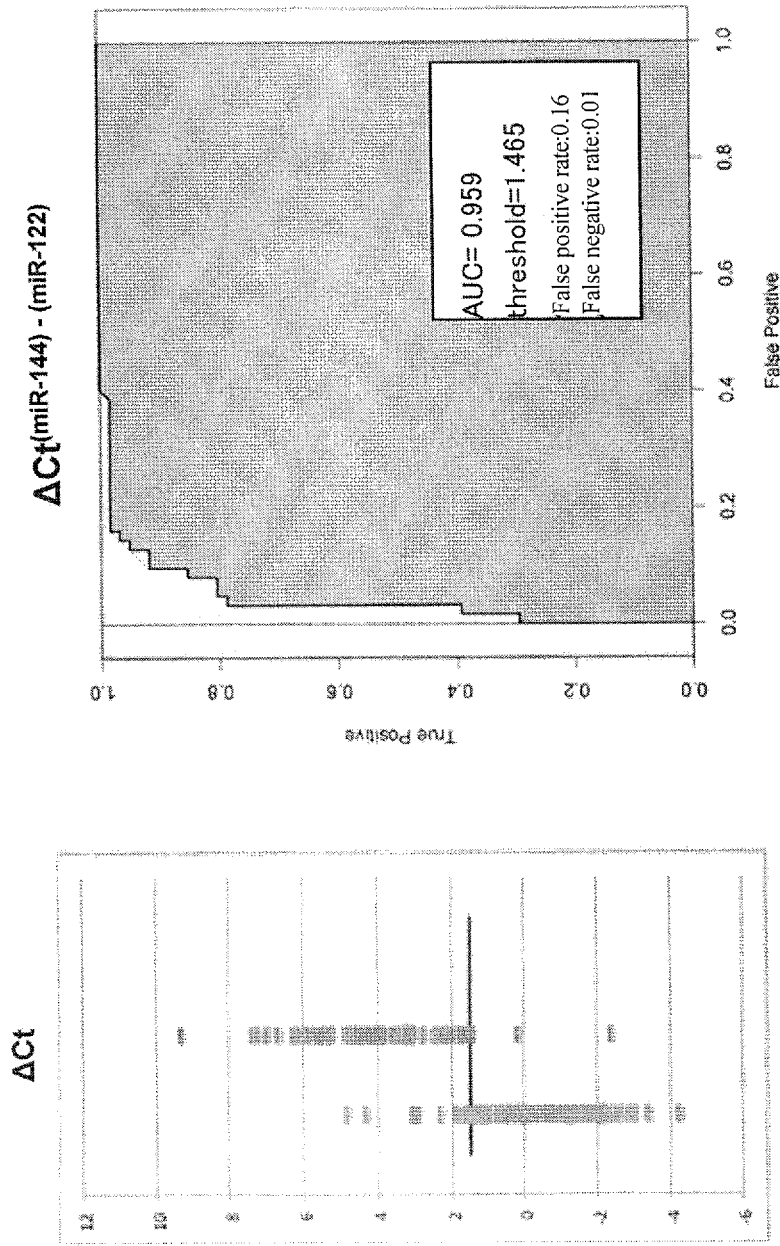
Fig.4-A

The expression distribution and the ROC curve of the combination of miR-122 and let-7f in Alzheimer's disease patients
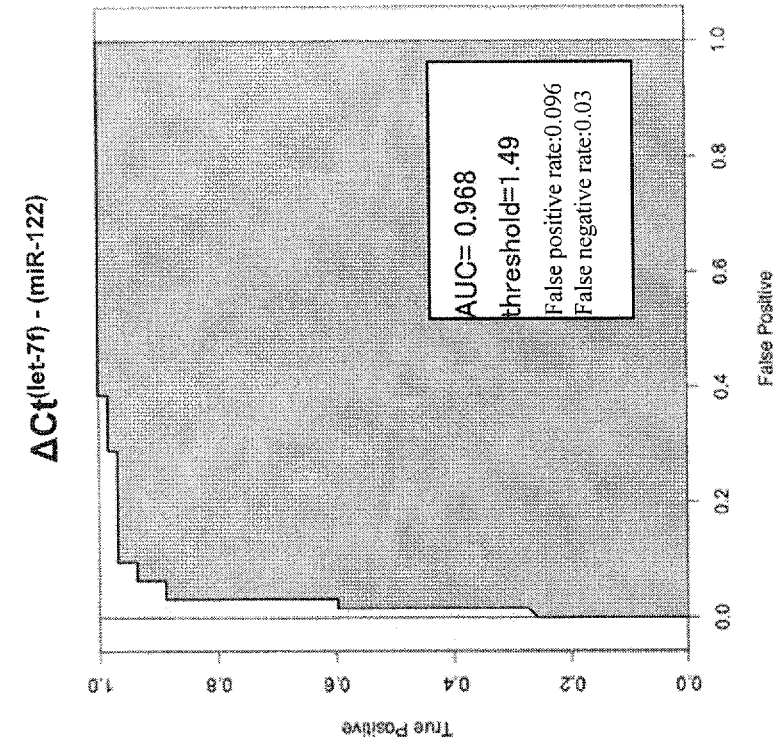
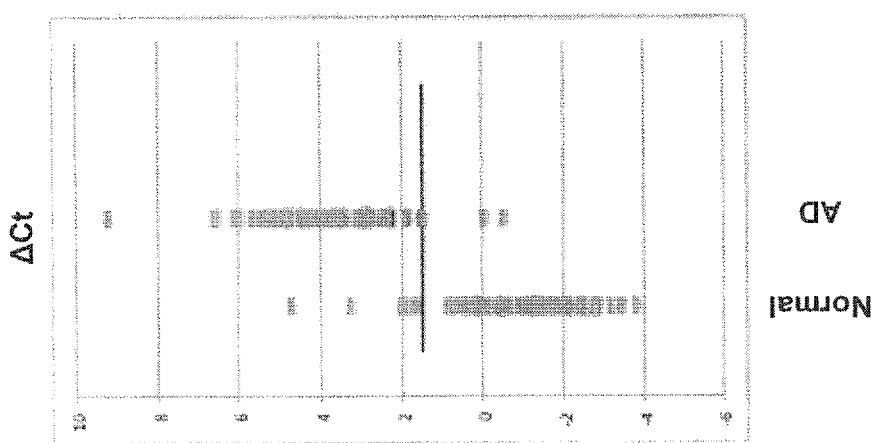
Fig.4-B

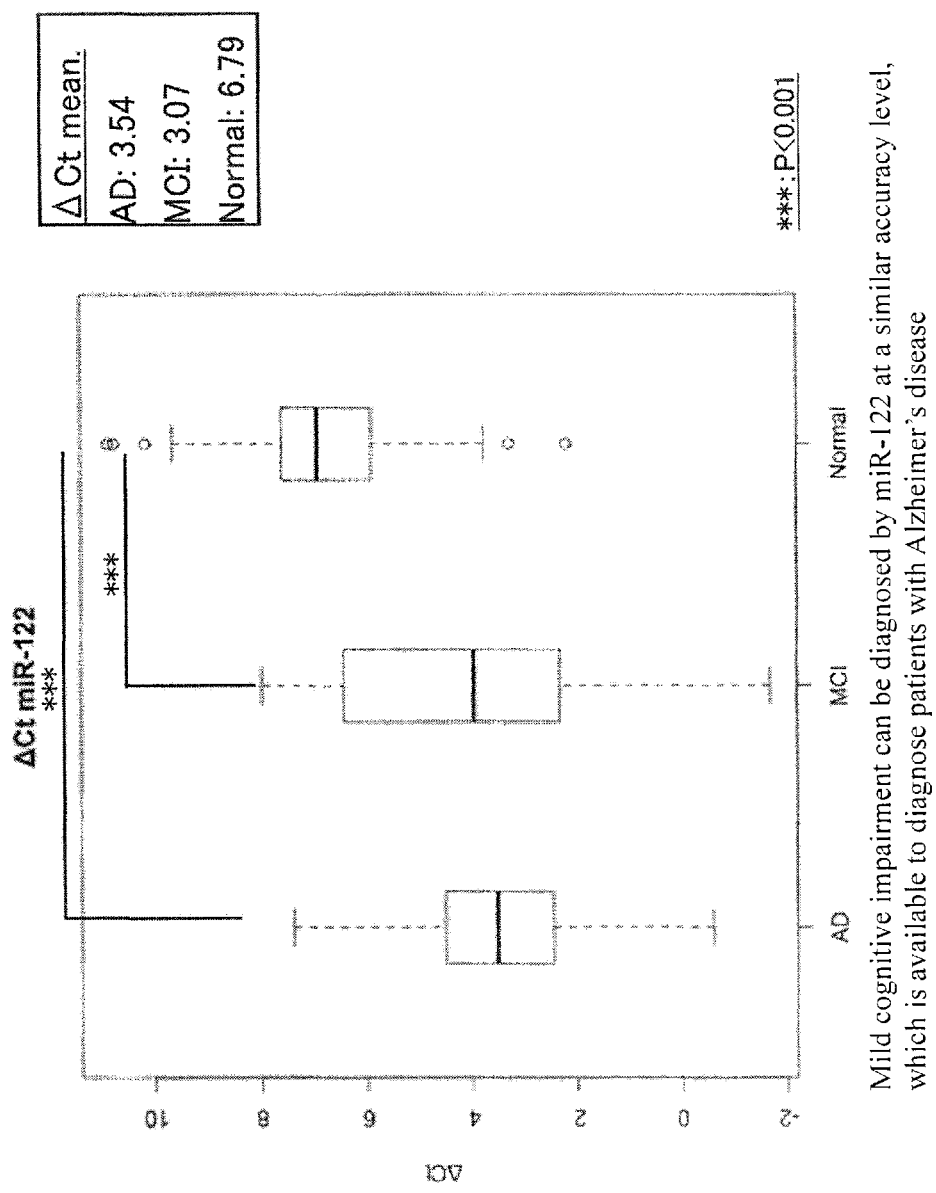
Fig.5-A

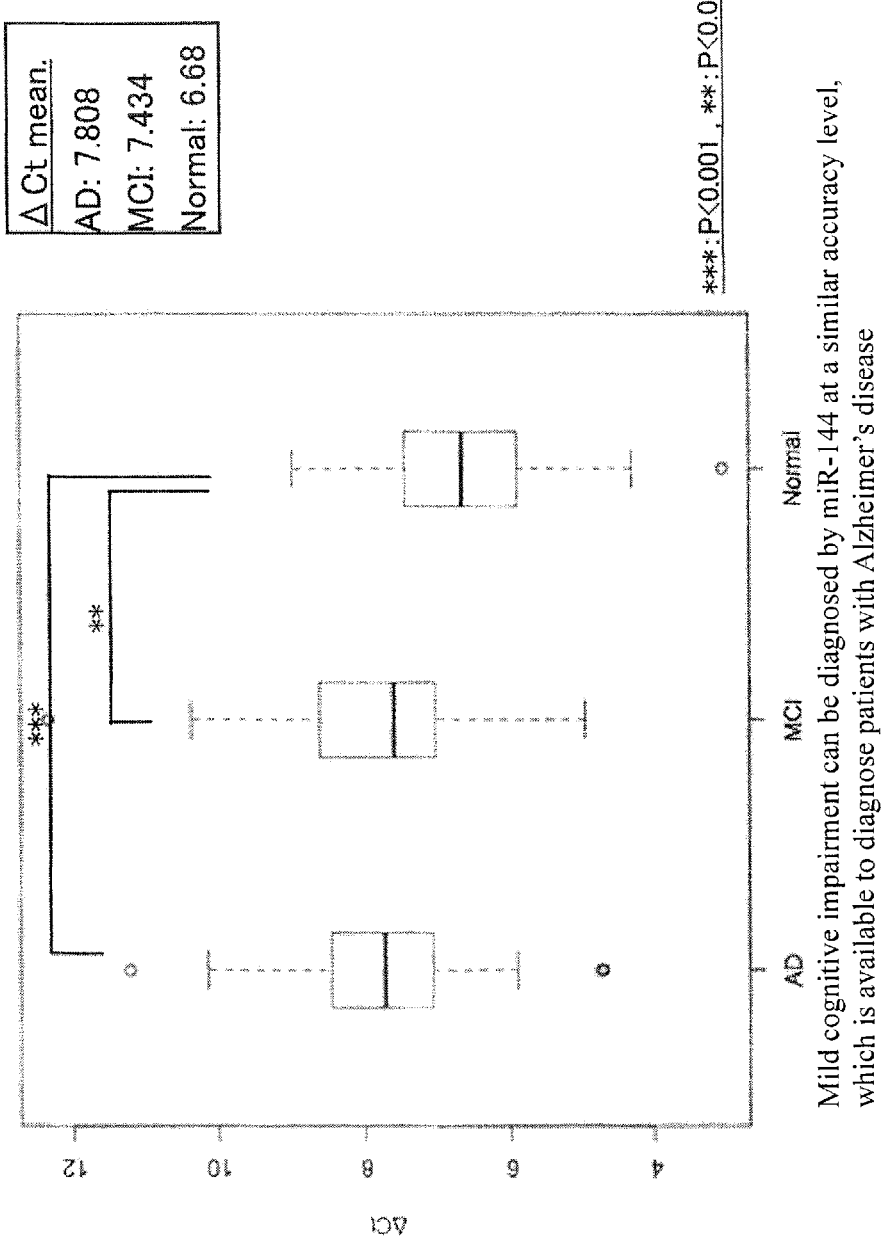
Fig.5-B

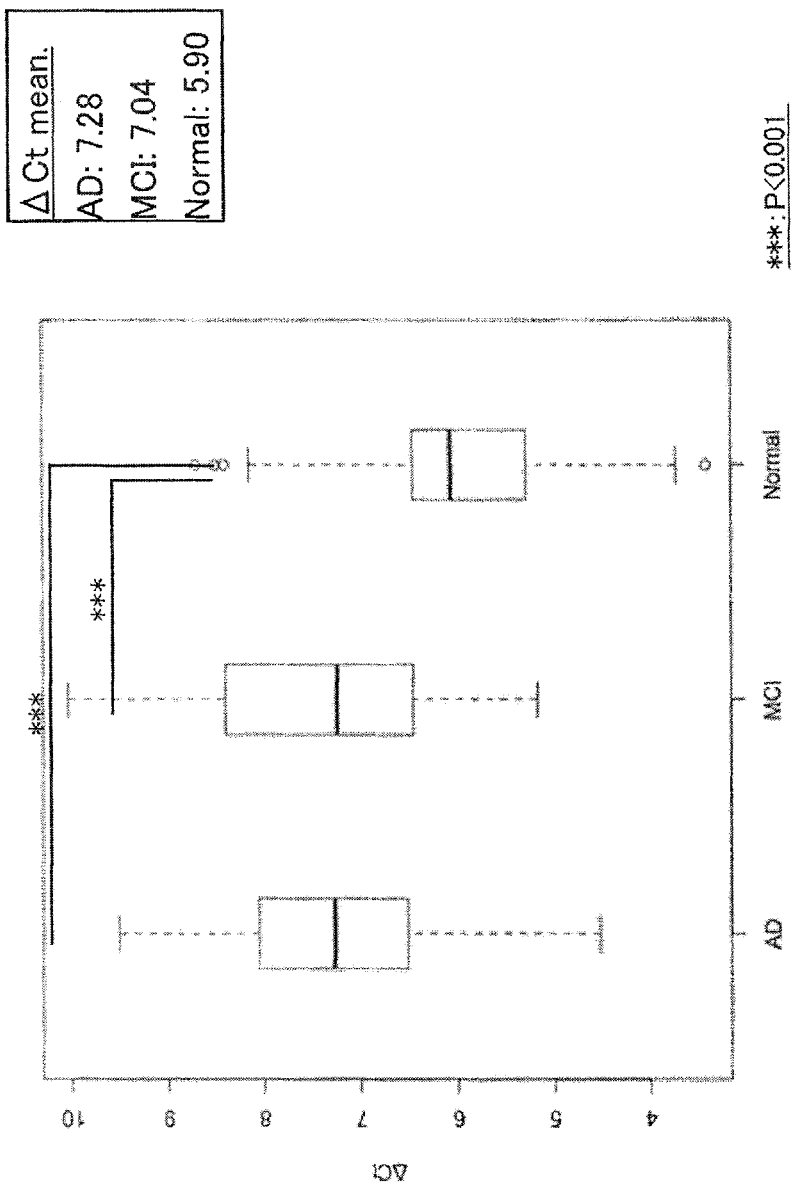
Fig.5-C

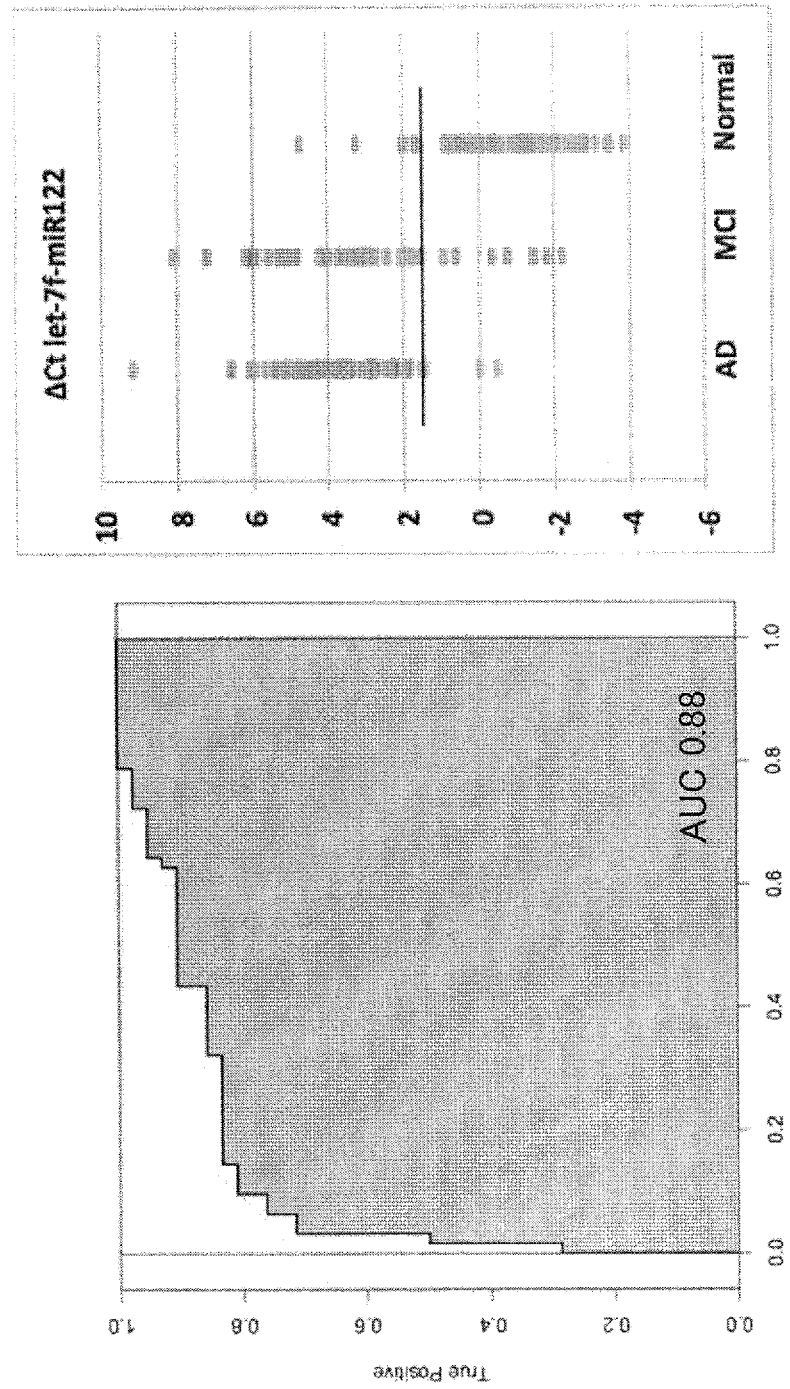
Fig.6-A

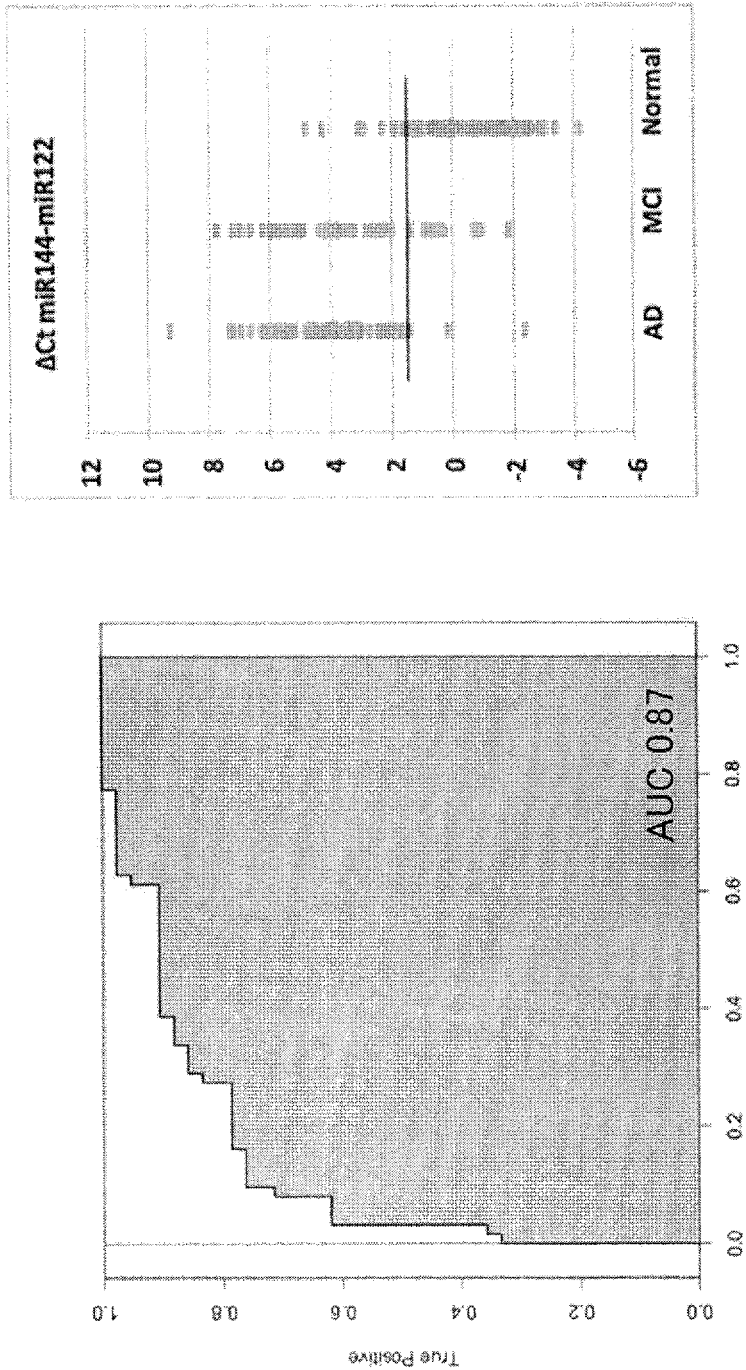
Fig.6-B

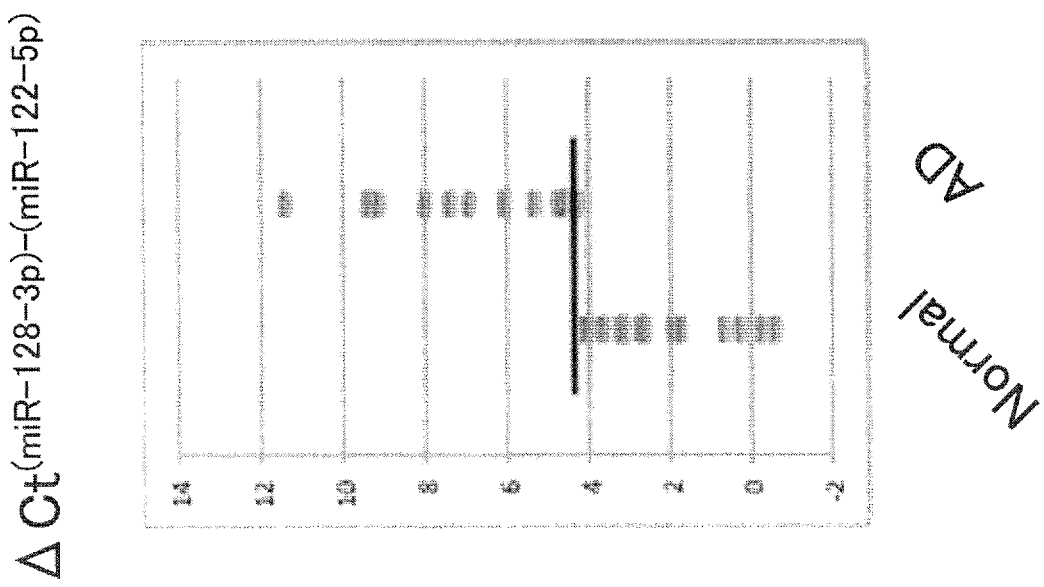
Fig.6-C

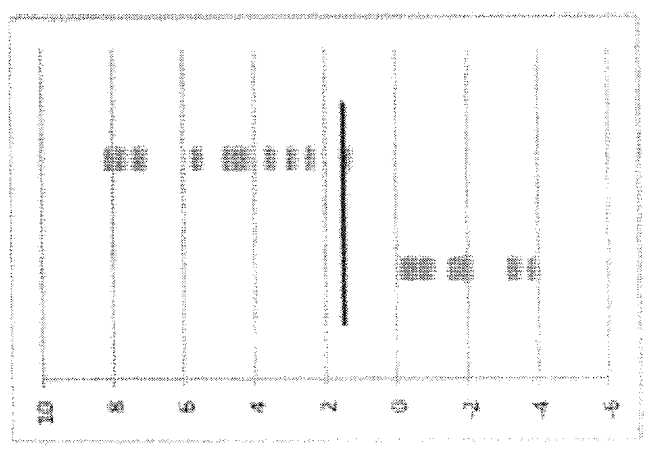
Fig.6-D

| Information about samples | | |
|---|---|---|
| Alzheimer's | Sample number 62 (Male 21, Female 41) | |
| | Average age 79.8 (Maximum 93, Minimum 56) | |
| MCI | Sample number 25 (Male 16, Female 9) | |
| | Average age 74.5 (Maximum 88, Minimum 53) | |
| Healthy individuals | Sample number 62 (Male 21, Female 41) | |
| | Average age 74.9 (Maximum 97, Minimum 51) | |

Fig.9

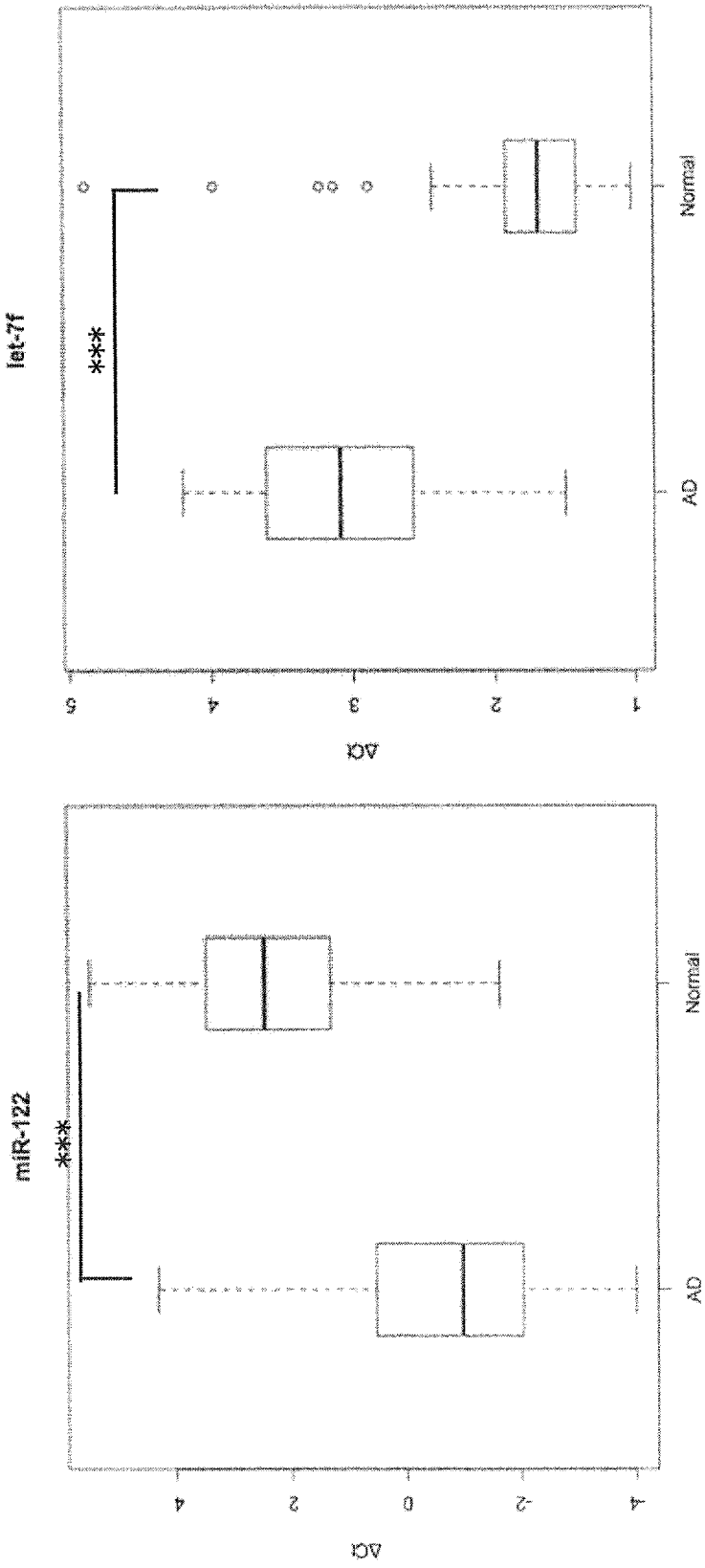
Fig.11-A

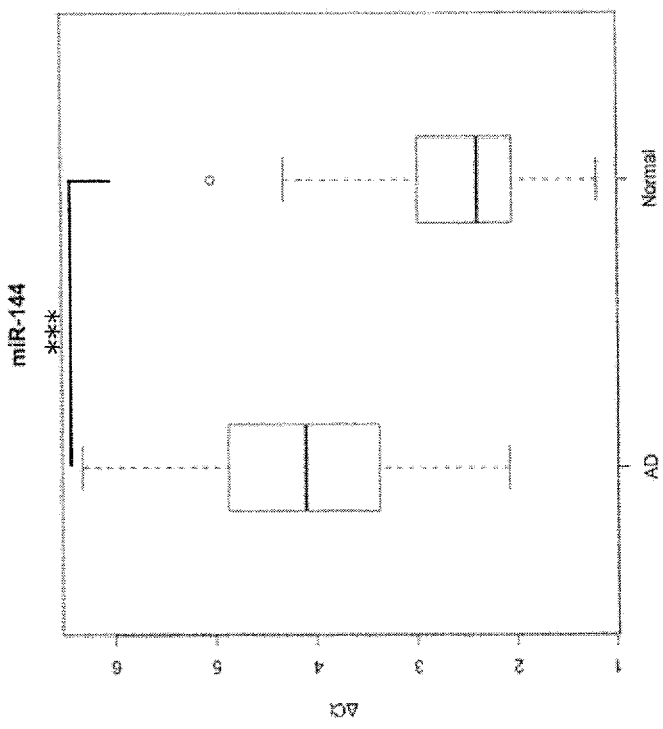
An advantage of using let7g as an internal control in the diagnosis using miR-144
The case where let-7g is used for the normalization to calculate ΔCt
(ΔCt = (candidate miR)−(let7g))
Fig.11-B

METHOD FOR ASSISTING DETECTION OF ALZHEIMER'S DISEASE OR MILD COGNITIVE IMPAIRMENT

TECHNICAL FIELD

The present invention relates to a method for assisting the detection of Alzheimer's disease or mild cognitive impairment.

BACKGROUND ART

Alzheimer's disease is the most common type of dementia, which accounts for more than half of cases, and the number of patients with this disease is expected to increase more and more in the elderly society in future. As a progressive disease, Alzheimer's disease cannot be fully cured or the progression of the disease cannot be completely blocked by current medical science, but medicines and medical treatments to slow down the progression are available. Thus, it is desirable to detect Alzheimer's disease as early as possible. In particular, since mild cognitive impairment (referred to as MCI) is often developed as a step prior to the onset of Alzheimer's disease, the detection of mild cognitive impairment can help prevent or slow down as much as possible the progression to Alzheimer's disease. Although Alzheimer's disease is currently diagnosed by means of medical interview, MRI scanning of the brain, and the like, it is not an easy task to detect early Alzheimer's disease or mild cognitive impairment.

Thus, to detect Alzheimer's disease at its early stage, methods in which the amount of microRNA (hereinafter referred to as "miRNA") in blood is used as an indicator are proposed (Patent Documents 1 to 3, Non-Patent Documents 1 to 3).

PRIOR ART REFERENCES

Patent Documents

Patent Document 1: Japanese Laid-open Patent Application (Kokai) No. 2014-132863.
Patent Document 2: Japanese Translated PCT Patent Application Laid-open No. 2014-520529.
Patent Document 3: EP 2733219 A1

Non-Patent Documents

Non-Patent Document 1: Pavan Kumar et al., PLOS ONE, July 2013, Volume 8, Issue 7, e69807, pp. 1-10.
Non-Patent Document 2: Petra Leindinger et al., Genome Biology 2013, 14: R78.
Non-Patent Document 3: Wang-Xia Wang et al., The Journal of Neuroscience, Jan. 30, 2008, 28(5): 1213-1223.

SUMMARY OF THE INVENTION

Problem to be Solved by the Invention

As described above, various miRNAs have been proposed as indices for the detection of Alzheimer's disease and, needless to say, it is advantageous if Alzheimer's disease can be detected with higher accuracy.

Thus, an object of the present invention is to provide a method for assisting the detection of Alzheimer's disease or mild cognitive impairment, the method for assisting the highly accurate detection of Alzheimer's disease or mild cognitive impairment.

Means for Solving the Problem

The inventors studied intensively and consequently found a specific miRNA whose amount was increased in Alzheimer's disease or mild cognitive impairment and various specific miRNAs whose amounts were decreased in Alzheimer's disease or mild cognitive impairment and discovered that Alzheimer's disease or mild cognitive impairment was successfully detected with high accuracy by using particular miRNAs among them as indices, and thereby completed the present invention.

That is, the present invention provides the following items.

(1) A method for assisting the detection of Alzheimer's disease or mild cognitive impairment, the method using as an indicator the amount of at least one miRNA selected from the group consisting of miR-122, miR-144, let-7f, miR-128-3p and miR-107 contained in a test sample separated from a living body, wherein a larger amount of miR-122 than that in a healthy individual, and/or a smaller amount of at least one miRNA selected from the group consisting of miR-144, let-7f, miR-128-3p and miR-107 than that in a healthy individual is indicative that the living body is more likely to have developed Alzheimer's disease or mild cognitive impairment, said method excluding the methods in which miR-144, let-7f, or miR-107 is used as a sole indicator.

(2) The method according to (1) for assisting the detection of Alzheimer's disease or mild cognitive impairment, wherein the amount of at least one miRNA selected from the group consisting of miR-122, miR-144 and let-7f contained in a test sample separated from a living body is used as an indicator.

(3) The method according to (1), wherein the amount of at least one selected from the group consisting of the combinations below is used as an indicator:
(I) miR-122 and miR-144;
(II) miR-122 and let-7f;
(III) miR-122 and miR-128-3p; and
(IV) miR-122 and miR-107.

(4) The method according to (3), wherein the amount of the combination (III) of miR-122 and miR-128-3p is used as an indicator.

(5) The method according to any of (1) to (4), wherein the test sample is serum or plasma.

(6) The method according to (5), wherein at least one microRNA selected from the group consisting of let-7g-5p, miR425-3p and miR425-5p is used as an internal control.

Effect of the Invention

According to the method of the present invention, Alzheimer's disease or mild cognitive impairment can be detected with high accuracy and yet conveniently. Thus, the method of the present invention will greatly contribute to the detection of Alzheimer's disease or mild cognitive impairment.

BRIEF DESCRIPTION OF THE DRAWINGS

FIGS. 1-A and 1-B show microRNAs in which a significant difference between Alzheimer's and healthy individual groups has been indicated by next-generation sequence analysis in the example below. The vertical axis represents the number of reads for each miRNA per million reads in total. Because the mature sequences of let-7f-1 and let-7f-2 are identical each other, they were used in the analysis as let-7f.

FIGS. 2-A and 2-B indicate the results of qRT-PCR data analysis using the ΔΔCt method in the example below. Seven out of 10 candidate miRNAs obtained by the next-generation sequence analysis indicated a significant difference.

FIGS. 3-A and 3-B show ROC curves and scatter plots of ΔCt values from each sample generated based on the results of qRT-PCR in the example below.

FIGS. 4-A and 4-B show scatter plots and ROC curves generated based on the calculated difference in ΔCt value between let-7f and miR-122 as well as the calculated difference in ΔCt value between miR-144 and miR-122 in the example below.

FIGS. 5-A to 5-C show box plots of ΔCt values of miR-122, let-7f, and miR-144 in the Alzheimer's group, the MCI group, and the normal individual group in the example below. A significant difference was observed between the MCI group and the healthy individual group at a level of P<0.05.

FIG. 6-A is a diagram showing the comparison of measurement results based on the formula ΔCt(let-7f)−(miR-122), wherein each value has been measured for the Alzheimer's disease group, the MCI group and the healthy individual group in the example below.

FIG. 6-B is a diagram showing the comparison of measurement results based on the formula ΔCt(miR-144)−(miR-122), wherein each value has been measured for the Alzheimer's disease group, the MCI group and the healthy individual group in the example below.

FIG. 6-C is a diagram showing the comparison of measurement results based on the formula ΔCt(miR-128-3p)−(miR-122-5p), wherein each value has been measured for the Alzheimer's disease group, the MCI group and the healthy individual group in the example below.

FIG. 6-D is a diagram showing the comparison of measurement results based on the formula ΔCt(miR-107)−(miR-122-5p), wherein each value has been measured for the Alzheimer's disease group, the MCI group and the healthy individual group in the example below.

FIG. 9 is a diagram depicting the information about samples in the example below.

FIG. 11-A is a diagram indicating the measurement results of miR-122 and let-7f obtained in the example below, which have been normalized with regard to ΔCt of let-7g used as an internal control.

FIG. 11-B is a diagram indicating the measurement results of miR-144 obtained in the example below, which have been normalized with regard to ΔCt of let-7g used as an internal control.

DETAILED DESCRIPTION OF THE INVENTION

Figure 7:
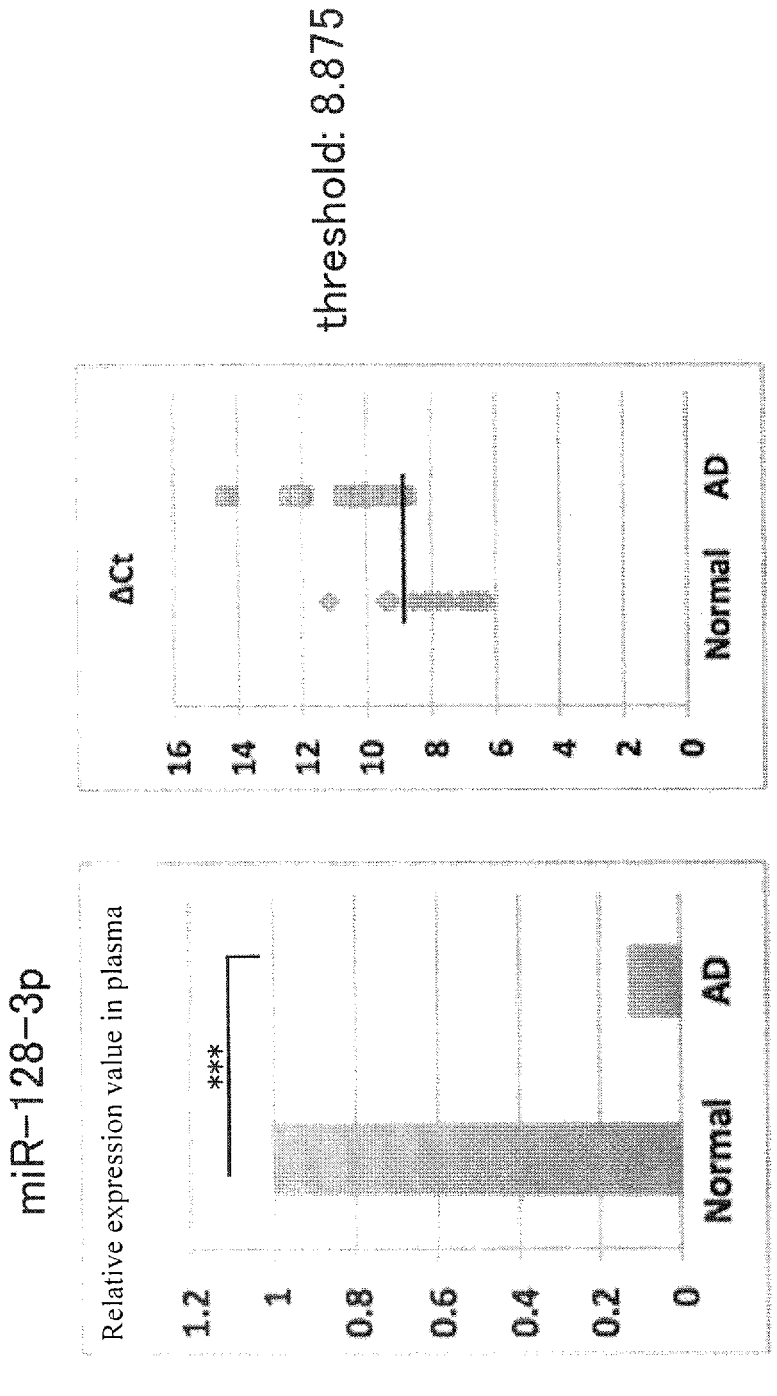
FIG. 7 is a diagram showing the measurement results for miR-128-3p which has been identified as a miRNA decreased in Alzheimer's disease in the example below.

As described above, in the method of the present invention, the amount of at least one miRNA selected from the group consisting of miR-122, miR-144, let-7f, miR-128-3p and miR-107 contained in a test sample separated from a living body is used as an indicator (the methods in which miR-144, let-7f, or miR-107 is used as a sole indicator are excluded). These miRNAs themselves are well known and the base sequences thereof are also well known. For the sake of confirmation, the base sequences of these miRNAs are indicated below:
miR-122: uggagugugacaaugguguuug (SEQ ID NO: 1);
miR-144: ggauaucaucauauacuguaag (SEQ ID NO: 2);
let-7f: ugagguaguagauuguauaguu (SEQ ID NO: 3);
miR-128-3p: ucacagugaaccggucucuuu (SEQ ID NO: 4);
miR-107: agcagcauuguacagggcuauca (SEQ ID NO: 5).

In these miRNAs, the amount of miR-122 is larger in patients with Alzheimer's disease or mild cognitive impairment than in normal individuals, while the amount of miR-144, let-7f, miR-128-3p and miR-107 is smaller in patients with Alzheimer's disease or mild cognitive impairment than in normal individuals.

These five miRNAs may be used individually or in combination and the combination use further increases the accuracy. In miR-144 and let-7f, whose amount is decreased in patients with Alzheimer's disease or mild cognitive impairment, at least one of these miRNAs is preferably used as an indicator together with miR-122, but either one of those miRNAs may be used as an indicator. By using as an indicator the amount of at least one combination selected from the group consisting of (I) miR-122 and miR-144, (II) miR-122 and let-7f, (III) miR-122 and miR-128-3p, and (IV) miR-122 and miR-107, a very high level of accuracy as indicated by an AUC (Area Under Curve) of the ROC (Receiver Operating Characteristic) curve of 0.9 is achieved, as specifically described in the Example below. In particular, a perfect result as indicated by an AUC of 1.00 is achieved by the combination (III) of miR-122 and miR-128-3p. An AUC of 1.00 represents a false positive rate of 0% and a false negative rate of 0% as well as the achievement of the highest accuracy.

The test sample is not particularly limited as long as it is a body fluid containing miRNAs, but typically a blood sample (including plasma, serum and whole blood) is preferably used.

The miRNA quantification method itself is well known and all the reagents and apparatus necessary for the quantification are commercially available, so that the quantification can be readily performed by those skilled in the art. One example is specifically described in the Example below. In the method described in the Example below, a poly-A tail is added to each miRNA at its 3' end by using commercially available reagents and the quantification of each miRNA is performed by quantitative real-time PCR (qRT-PCR) using an oligonucleotide as a reverse primer that hybridizes to the added region (that is, poly-T) and an oligonucleotide as a forward primer that hybridizes to each miRNA (the complementary strand of each miRNA). Each miRNA can be easily quantified by this method, though the quantification method is not limited thereto, and likewise quantified, for example, by a method using a commercially available so-called "next-generation sequencer," and the like.

As the test sample, a blood sample can preferably be used as described above, and serum and plasma can particularly preferably be used. In cases where the above-described miRNAs in serum or plasma are measured, at least one microRNA selected from the group consisting of let-7g-5p, miR425-3p and miR425-5p is preferably used as an internal control, which is a miRNA with a little variation in amount in the serum and plasma.

In the method of the present invention, if the amount of miR-122 is larger than that in healthy individuals and/or the amount of at least one miRNA selected from the group consisting of miR-144, let-7f, miR-128-3p and miR-107 is smaller than that in healthy individuals, it is judged as suggesting a high possibility of Alzheimer's disease or mild cognitive impairment. Because a statistically significant difference (in Examples, $p<0.001$ or $p<0.01$ in t-test) is observed for each miRNA used herein between patients with Alzheimer's disease or mild cognitive impairment and healthy individuals even when it is used individually, the presence or absence of a statistically significant difference ($p<0.05$, preferably $p<0.01$, further preferably $p<0.001$ in t-test) from healthy individuals is preferably used as a criterion. Specifically, as shown in the Example below, preferably, if the ΔCt value (the cut-off value) in the combination of miR-122 and let-7f (ΔCt(let-7f)−(miR-122)) at a plot point corresponding to the best value (the lowest value) for the false positive rate is, for example, not less than 1.49, it is judged as suggesting a high possibility of Alzheimer's disease or mild cognitive impairment (see FIG. 4-B). Alternatively, as described above, a combination of miR-122, which increases in Alzheimer's disease or mild cognitive impairment, and miR-144, let-7f, miR-128-3p, or miR-107, which decreases in Alzheimer's disease or mild cognitive impairment, as shown below is preferably used as an indicator:

ΔCt(miR-144)−(miR-122);
ΔCt(let-7f)−(miR-122);
ΔCt(miR-128-3p)−(miR-122); or
ΔCt(miR-107)−(miR-122).

The present invention will be specifically described below by way of examples. Of course, the present invention will not be limited by the example below.

EXAMPLES

Materials and Methods
Section 1. Clinical Samples
Subsection 1. Used Clinical Samples Peripheral blood was collected based on the plan for a human genome and gene analysis research approved by the Ethics Committee of Hiroshima University for Human Genome and Gene Analysis Research. The details of the peripheral blood used for the analysis in this Example will be shown in the table below.

Subsection 2. Recovery of Plasma from Whole Blood and Preservation of the Plasma 1) Five mL of whole blood collected in a VENOJECT II vacuum blood collection tube supplemented with EDTA-2K was transferred to a 15-mL tube and centrifuged at 3500 rpm for 10 minutes at room temperature.
2) The centrifugation produces three layers separated in the following order from the top: plasma layer, white blood cell layer, and red blood cell layer. Among those layers, only the plasma layer was transferred to a new 2-mL tube.
3) The collected plasma in the step 2 was centrifuged at 10000 rpm for 10 minutes at room temperature to precipitate blood cell components contaminated therein.
4) Only the plasma layer was dispensed in 250-μL aliquots into new 1.5-mL tubes and frozen at −80° C. for preservation.

Section 2. Extraction of RNA in Plasma

Extraction of RNA in plasma was performed using the miRNeasy Mini kit (QIAGEN).
1) The frozen plasma sample was thawed and centrifuged at 10000 rpm for 5 minutes at room temperature to precipitate aggregated proteins and blood cell components.
2) To a new 1.5-mL tube, 200 μL of the supernatant was transferred.
3) To the tube, 1000 μL of the QIAzol Lysis Reagent was added and the resultant was mixed thoroughly to denature protein components.
4) To the tube, 10 μL of 0.05 nM cel-miR-39 was added as a control RNA for RNA extraction and the resultant was mixed by pipetting and then left to stand at room temperature for 5 minutes.
5) To promote the separation of aqueous and organic solvent layers, 200 μL of chloroform was added to the tube and the resultant was mixed thoroughly and left to stand at room temperature for 3 minutes.
6) The tube was centrifuged at 12000×g for 15 minutes at 4° C. and 650 μL of the upper aqueous layer was transferred to a new 2-mL tube.
7) For the separation of RNA, 975 μL of 100% ethanol was added to the tube and the resultant was mixed by pipetting.
8) To a miRNeasy Mini spin column (hereinafter referred to as column), 650 μL of the mixture in the step 7 was transferred and left to stand at room temperature for 1 minute and then centrifuged at 8000×g for 15 seconds at room temperature to allow RNA to be adsorbed on the filter of the column. The flow-through solution from the column was discarded.
9) The step 8 was repeated until the total volume of the solution of the step 7 was filtered through the column to allow all the RNA to be adsorbed on the filter.
10) To remove impurities attached on the filter, 650 μL of Buffer RWT was added to the column and centrifuged at 8000×g for 15 seconds at room temperature. The flow-through solution from the column was discarded.
11) To clean the RNA adsorbed on the filter, 500 μL of Buffer RPE was added to the column and centrifuged at 8000×g for 15 seconds at room temperature. The flow-through solution from the column was discarded.
12) To clean the RNA adsorbed on the filter, 500 μL of Buffer RPE was added to the column and centrifuged at 8000×g for 2 minutes at room temperature. The flow-through solution from the column was discarded.
13) To completely remove any solution attached on the filter, the column was placed in a new 2-mL collection tube and centrifuged at 10000×g for 1 minute at room temperature.
14) The column was placed in a 1.5-mL tube and 50 μL of RNase-free water was added thereto and the resultant was left to stand at room temperature for 1 minute.
15) Centrifugation was performed at 8000×g for 1 minute at room temperature to elute the RNA adsorbed on the filter. The eluted RNA was used in the following experiment without further purification and the remaining portion of the eluted RNA was stored at −80° C.

Section 3. Analysis of MicroRNA in Plasma
Subsection 1. Comprehensive Analysis on Next-Generation Sequencer In this Example, the concentration of the RNA solution was not adjusted because the amount of RNA extractable from the plasma was very small and therefore the determination of the concentration was difficult. Accordingly, the analysis compared samples not with regard to "how much amount of a miRNA of interest had been contained in the same mass of RNA" but with regard to "how much amount of a miRNA of interest had been contained in a solution of RNA extracted from the same volume of plasma". This is also applicable to the subsequent qRT-PCR analysis.

Analysis by a next-generation sequencer was performed using the Ion Total RNA-seq Kit v2, the Ion PGM (Life Technologies), and the Bioanalyzer (Agilent).

A 50-µL solution containing the plasma-derived microRNAs extracted in Section 2 is concentrated under vacuum to 10 µL.

For adaptor hybridization, to 4 µL of the RNA solution concentrated in 1), 1 µL of Ion Adoptor Mix v2 and 3µL of Hybridization buffer are added.

This is mixed by slowly pipetting up and down 10 times and then spun down.

The reaction is allowed to proceed at 65° C. for 10 minutes and then at 16° C. for 5 minutes in a thermal cycler.

For adaptor ligation, to the reaction solution of 4), 10 µL of 2× Ligation buffer and 2 µL of Ligation Enzyme Mix are added.

This is gently mixed by pipetting up and down, and then spun down.

The reaction is allowed to proceed at 16° C. for 16 hours in a thermal cycler.

For reverse transcription of the adaptor-ligated microRNAs, to the solution of 7), 2 µL of Nuclease-Free water, 4 µL of 10× RT buffer, 2 µL of 2.5 mM dNTP Mix, and 8 µL of Ion RT Primer v2 are added.

This is gently mixed by pipetting up and down, and then spun down.

The reaction is allowed to proceed at 70° C. for 10 minutes in a thermal cycler.

The reaction solution is immediately placed on ice and supplemented with 4 µL of 10× SuperScript III Enzyme Mix.

This is gently mixed by pipetting up and down, and then spun down.

The reaction is allowed to proceed at 42° C. for 30 minutes in a thermal cycler.

Nucleic acids with a length similar to that of the cDNA of interest are extracted by beads purification. Nucleic Acid Binding Beads are gently vortexed.

On a Plocessing Plate, 5 µL of the Nucleic Acid Binding Beads is applied to each well.

To each well of 15), 250 µL of Binding Solution Concentrate is added and mixed by pipetting up and down 10 times.

To the cDNA solution of 13), 60 µL of Nuclease-Free water is added.

The solution of 17) is added to the mixture of 16).

A P-1000 pipettor is set at 275 µL and a pipette tip is rinsed three times with 100% ethanol.

The pipette tip of 19) is directly used to add 275 µL of 100% ethanol to the solution of 17) and to mix the solution by pipetting up and down 10 times.

The mixture is left to stand at room temperature for 5 minutes.

The Processing Plate is left to stand for 5 minutes on a magnetic stand.

The supernatant is discarded from the plate, and then the Nucleic Acid Binding Beads are air-dried for 2 minutes while leaving the plate on the magnetic stand.

The Processing Plate is removed from the magnetic stand and 13 µL of Nuclease-Free water is added thereto and then the resultant is mixed by pipetting up and down 10 times.

The mixture is left to stand at room temperature for 1 minute.

The Processing Plate is placed on the magnetic stand for 1 minute and then 13 µL of the solution is recovered.

For amplification of the purified cDNA, 6 µL of the cDNA solution of 26) is dispensed into a 0.2-mL tube.

To the tube of 27), 45 µL of Platinum PCR SuperMix High Fidelity, 1 µL of Ion Xpress RNA-Seq Barcode, and 1 µL of Ion Xpress RNA 3' Barcode Primer are added.

The reaction was allowed to proceed in a thermal cycler under the conditions below:
  94° C. for 2 minutes;
  (2 cycles) 94° C. for 30 seconds, 50° C. for 30 seconds, and 68° C. for 30 seconds;
  (19 cycles) 94° C. for 30 seconds, 62° C. for 30 seconds, and 68° C. for 30 seconds; and
  68° C. for 5 minutes.

For removal of adaptor dimers, the amplified cDNAs are electrophoresed on a gel, and a part thereof is excised. A 10% TBE acrylamide gel is prepared and run at 120V. 1× TBE was used as a running buffer.

In a Tupperware container, 20 mL of 1× TBE and the 10% TBE acrylamide gel of 30) are placed.

To the container, 2 µL of SYBR gold is added and the container is shaken for 5 minutes.

A DNA band around 100 to 106 bp is excised under UV illumination.

The excised gel is transferred into a 1.5-mL tube and moderately crushed with the tip of a pipette tip.

To the tube, 500 µL of TE buffer is added.

Incubation is performed at 37° C. overnight.

Centrifugation is performed at 3000 rpm for 3 minutes.

The supernatant is transferred into a new 1.5-mL tube and 1 µL of 20 mg/mL glycogen is added thereto as a coprecipitating agent.

To the tube, 50 µL of 3M sodium acetate is added.

To the tube, 400 µL of isopropanol is added and vortexed.

The tube is left to stand at −80° C. for 30 minutes.

Centrifugation is performed at 15,000×g for 30 minutes at 4° C.

The supernatant is discarded from the tube and 1 mL of 70% ethanol is added thereto.

Centrifugation is performed at 15,000×g for 5 minutes at 4° C.

The supernatant is discarded from the tube and the tube is air-dried.

To the tube, 15 µL of Nuclease-Free water is added.

The measurement of concentration is performed using the DNA High Sensitivity Kit on the Bioanalyzer.

The cDNA sample is diluted to a concentration of 20 pM to perform emulsion PCR.

The Ion OneTouch 2 (Life Technologies) was used for the emulsion PCR.

Recovery tubes and an Amplification Plate are installed into the Ion OneTouch 2.

A Reagent tube is half-filled with the Oil and another Reagent tube is quarter-filled with the Recovery Solution, and then they are installed into the Ion OneTouch 2.

In a 1.5-mL low-binding tube, 25 µL of the cDNA diluted in 48), 25 µL of Nuclease-Free water, 500 µL of Reagent Mix, 300 µL of PCR Reagent B, and 50 µL of Enzyme mix are mixed.

Ion Sphere Particles are vortexed, spun down, and then added in 100 µL to the mixture of 51).

The mixture is vortexed and then spun down.

The Reaction Filter Assembly is filled with the reaction mix and installed into the Ion OneTouch 2, and then emulsion PCR is started.

An emulsion PCR sample is recovered and purified by beads purification using the Ion One Touch ES (Life Technologies).

The sample is recovered and the entire volume of the sample is transferred to a 0.2-mL tube.

To the tube, 5 µL of Control Ion Sphere is added.

Centrifugation is performed at 15,500×g for 2 minutes.

The supernatant is discarded leaving 15 µL in the tube.

To the tube, 12 µL of Sequencing Primer is added.

The reaction is allowed to proceed at 95° C. for 2 minutes and then at 37° C. for 2 minutes in a thermal cycler. After the reaction, the temperature is returned to room temperature.

The sample is loaded onto a 318 Chip.

The chip is installed into the Ion PGM and the analysis is performed.

Subsection 2. Analysis of the Results

The analysis was performed using the CLC bio Genomics Workbench. The number of reads for each microRNA is normalized to the number of reads per million reads in each sample. A t-test was performed for each microRNA between the Alzheimer's group and the normal individual group, and microRNAs identified to show a difference at a level of P<0.05 and to have an average read count of not less than 50 in at least one group were selected for further analysis by qRT-PCR below.

Section 4. Quantification of MicroRNA in Plasma by qRT-PCR

Comprehensive analysis of miRNAs in plasma shown in Subsection 1 was performed using the miRCURY LNA™ Universal RT microRNA PCR, Universal cDNA synthesis kit II, and LightCycler480 multi-well plate (Exiqon).

The Universal cDNA synthesis kit II is a cDNA synthesis kit for miRNA designed to allow all miRNAs in a sample to be reverse-transcribed in one tube through the addition of poly-A tail to the 3' end of mature miRNA and the reverse transcription using a primer including a poly-T primer.

A PCR reaction starts and proceeds by addition of the synthesized cDNA and the SYBR Green master mix, a reaction reagent in which a fluorescent material and an enzyme are mixed, and primers to a LightCycler480 multi-well plate set and it allows the amount of a miRNA in the sample to be determined as the difference between fluorescence intensities. The second derivative method was used in the calculation of a Ct value, with which the Ct value is determined to correspond to a point showing the maximum change of fluorescence in the amplification curve, while the ΔΔCt method was used for the analysis, in which the amounts of miRNAs are relatively compared without generating a standard curve.

Subsection 2. Reverse Transcription of MicroRNA

Reverse transcription of miRNAs in plasma was performed using the Universal cDNA Synthesis Kit II (EXIQON).

1) Into a 0.2-mL tube, 2 µL of 5× Reaction buffer, 5 µL of Nuclease-Free water, 1 µL of Enzyme mix, and 2 µL of a solution of plasma-derived RNA are dispensed.
2) The mixture is mixed by tapping the tube and then spun down.
3) The reaction was allowed to proceed at 42° C. for 60 minutes and then at 95° C. for 5 minutes in a thermal cycler.
4) The synthesized cDNA was transferred to a 1.5-mL tube and stored at −80° C.

Subsection 3. qRT-PCR with SYBR Green

A real-time PCR reaction was performed using the LightCycler (trade name) 480 (Roche), the miRCURY LNA™ Universal RT microRNA PCR (EXIQON), and the LightCycler (trade name) 480 Multiwell Plate 384, white (Roche) for a 384-well plate. The PCR reaction mix and the diluted cDNA were dispensed to the 384-well plate using the Bravo Automated Liquid Handling Platform (Agilent Technologies).

1) The synthesized cDNA was diluted 40 times in DNase-free water in a 0.65-mL tube.
2) A PCR reaction mix was prepared in a 0.65-mL tube as indicated below (the indicated amounts are per one sample in a single replicate):
PCR master mix, 5 µL; PCR primer mix, 1 µL.
3) The PCR reaction mix was dispensed at 6 µL per well into the 384-well plate.
4) The diluted cDNA prepared at 1) was dispensed at 4 µL per well into the 384-well plate and mixed thoroughly by pipetting.
5) The 384-well plate was sealed to prevent evaporation of the sample and centrifuged at 1500×g for 1 minute at room temperature.
6) Real-time PCR was performed using the LightCycler (trade name) 480 (Roche) under the conditions below:
95° C. for 10 minutes;
(45 Cycles) 95° C. for 10 seconds and 60° C. for 1 minute.

Subsection 4. Analysis of the Results

The second derivative method was used in the calculation of a Ct value, with which the Ct value is determined to correspond to a point showing the maximum change of fluorescence in the amplification curve, while the ΔΔCt method was used for the analysis, in which the amounts of miRNAs are relatively compared without generating a standard curve. Moreover, as the amount of miRNA should be normalized to make comparison among samples, the external control cel-miR-39 added in 4) in the section 2 was used for the normalization. A method to calculate a normalized value (ΔCt value) is shown below:

$$\Delta Ct = Ct - Ct_{cel-miR-39}.$$

In the qRT-PCR analysis, a ΔCt value obtained by subtracting the Ct value of cel-miR-39 contained in a measured sample from a Ct value in the same sample according to the above formula was used for analysis.

Evaluation of the Accuracy of Marker MicroRNAs Based on ROC Curve

A method comprising plotting a ROC (Receiver Operating Characteristic) curve and calculating the AUC for comparison purpose is a method to evaluate the accuracy of a diagnostic marker. ROC represents a curve obtained by plotting "1—Specificity" (false positive rate) on the horizontal axis and "Sensitivity" on the vertical axis for varying a cut-off value that determines positive and negative outcomes, as a parameter. AUC (Area Under Curve) refers to the area under the ROC curve, which ranges from 0.5 to 1. When a ROC curve is generated and an AUC is calculated by using a certain diagnostic marker, an AUC value closer to 1 means that the diagnostic marker is evaluated as a more accurate marker. In general, a diagnostic marker with an AUC of ≥0.7 is considered to be with high accuracy.

Results

Section 1. Identification of MicroRNAs in Plasma that Exhibit a Variation Specific for Alzheimer's Disease Patients Subsection 1.

In this section, the miRNA profiles in the plasma from healthy individuals and Alzheimer's disease patients were comprehensively analyzed and compared to identify miRNAs that were variable in Alzheimer's disease patients.

Subsection 2. Comprehensive Analysis and Comparison of MicroRNAs in the Plasma from Healthy Individuals and Alzheimer's Disease Patients
(First Screening)

The amount of each miRNA in plasma was comprehensively analyzed in 62 individuals each from the healthy individual group and the Alzheimer's disease patient group by using the next-generation sequencer Ion PGM (Life Technologies), and then the amount of each miRNA in the groups was compared with each other. The mean value of the amount of each miRNA was calculated for each group and compared between the groups (FIGS. 1-A and 1-B).

Three miRNAs were identified as those with a significantly increased amount in the Alzheimer's disease patient group relative to the healthy individual group, while seven miRNAs were identified as those with a significantly decreased amount in the Alzheimer's disease patient group (FIGS. 2-A and 2-B).

These 10 miRNAs were considered as marker candidate miRNAs for Alzheimer's disease to be analyzed by qRT-PCR. Those miRNAs are described below.

MiRNAs whose amount in plasma was increased in the Alzheimer's disease patients relative to the healthy individuals: miR-122-5p, miR-185-5p.

MiRNAs whose amount in plasma was decreased in the Alzheimer's disease patients relative to the healthy individuals: let-7f-5p, let-7g-5p, miR-15b-5p, miR-30b-5p, miR-484-5p, miR-660-5p, miR-144-5p.

Subsection 3. Comparison of the Amount of Marker Candidate MicroRNAs between Healthy Individuals and Alzheimer's Disease Patients by qRT-PCR
(Second Screening)

The difference between the healthy individuals and the Alzheimer's disease patients demonstrated in the first screening with respect to the amount of miRNA in plasma is considered to be substantially influenced by individual differences in each sample used in the experiment. Then, in order to eliminate the influence of the individual differences on the amount of each marker candidate miRNA in plasma, the sample number was increased to 62 in each of the healthy individual group and the Alzheimer's disease patient group and, as the second screening, the amount of the individual candidate miRNA in the plasma of each sample was measured by qRT-PCR. The determination of the amounts of the marker candidate miRNAs in the second screening was performed by the qRT-PCR method using SYBR Green.

In each sample, ΔCt values were calculated and analyzed by t-test at a significance level of 5%. Among the 10 marker candidate miRNAs, a significant difference was observed for seven species consisting of miR-122, miR-185, let-7f, miR-15b, miR-484, and miR-144 between the healthy individual group and the Alzheimer's group. No significant difference was observed for the other three. Moreover, when ROC curves were generated by using the ΔCt values of these seven miRNAs, patients were successfully diagnosed with Alzheimer's disease by means of miR-122, let-7f, or miR-144 at an accuracy level indicated by an AUC of ≥0.8 (FIGS. 3-A and 3-B). Alternatively, when differences in ΔCt value between miR-122 and let-7f and between miR-122 and miR-144 were calculated and then ROC curves were generated again, it enabled the diagnosis more accurately at a level indicated by an AUC of >0.9 (FIGS. 4-A and 4-B).

Accordingly, miR-122 whose amount is increased in Alzheimer's disease patients as well as let-7f and miR-144 whose amount is decreased were successfully identified as marker candidate miRNAs.

Subsection 4. Comparison of the Amounts of Marker Candidate MicroRNAs between Healthy Individuals and Mild Cognitive Impairment (MCI) Patients by qRT-PCR A similar analysis by qRT-PCR was performed on miR-122, let-7f, and mir-144, which had been identified in Subsection 3 as candidate miRNAs for the diagnosis of Alzheimer's disease. When ΔCt values were calculated in 42 MCI patients and analyzed against the healthy individual group by t-test, a significant difference was observed at a level of P<0.05. A similar tendency to that in the Alzheimer's disease patients, including the upward tendency in miR-122 and the downward tendency in let-7f and miR-144, was also observed in the MCI patients (FIGS. 5-A, 5-B, and 5-C).

Subsection 5. Combinations of MiRNAs

The accuracy achieved by combining two different miRNAs was examined. Specifically the following experiment was performed. An analysis by qRT-PCR was performed on the samples used in Subsections 3 and 6 to calculate ΔCt values. Then, the differences in ΔCt value between two miRNAs, including ΔCt(let-7f)−(miR-122), ΔCt(miR-144)−(miR-122), ΔCt(miR-128-3p)−(miR-122-5p), and ΔCt(miR-107)−(miR-122-5p), were calculated. The results are separately shown in FIGS. 6-A to 6-D.

Figure 8:
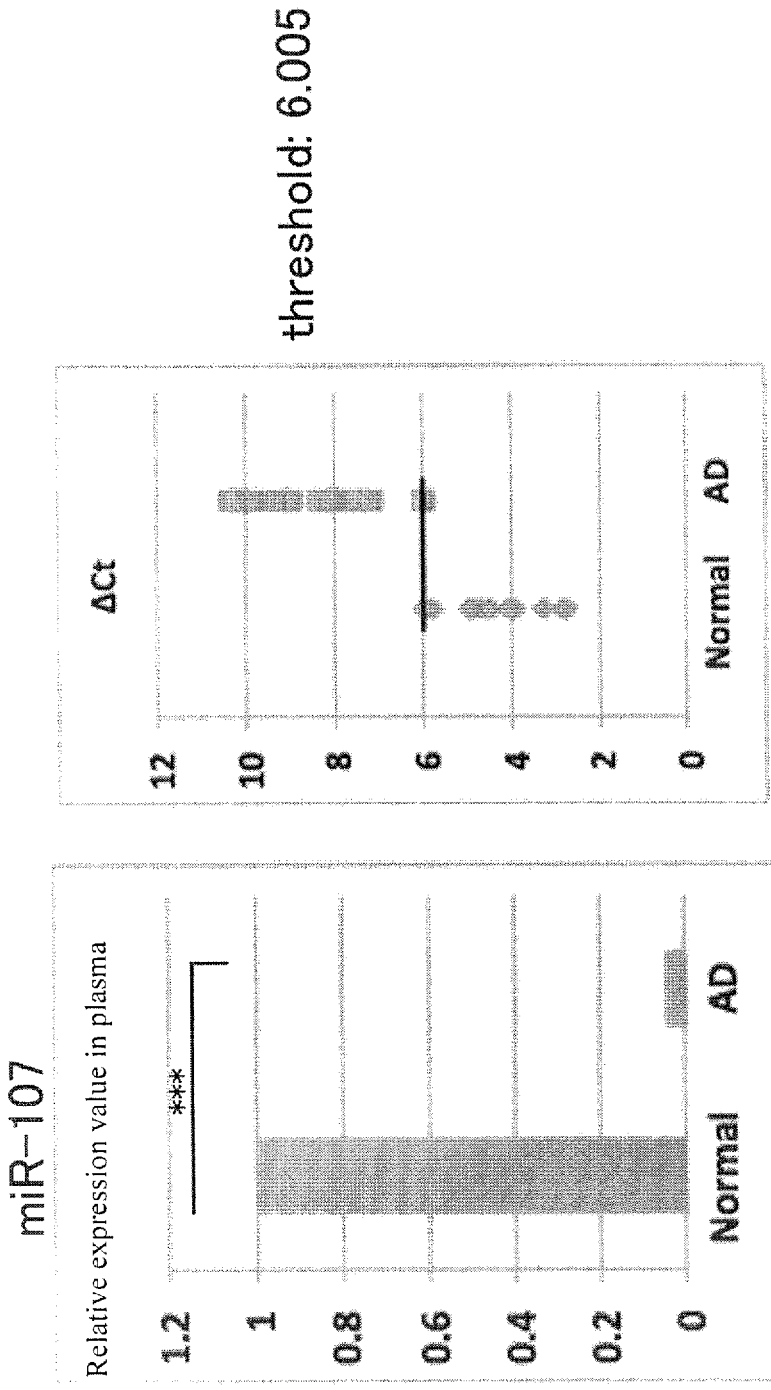
FIG. 8 is a diagram showing the measurement results for miR-107 which has been identified as a miRNA decreased in Alzheimer's disease in the example below.

Subsection 6. Identification of MicroRNAs Decreased in Alzheimer's Disease by Comprehensive qRT-PCR Analysis The above-described comprehensive qRT-PCR analysis identified miR-128-3p and miR-107 as microRNAs decreased in Alzheimer's disease. The results are separately shown in FIGS. 7 and 8. Moreover, the information about the samples is shown in FIG. 9.

Subsection 7. An Advantage of Let-7g as an Internal Control

Figure 10:
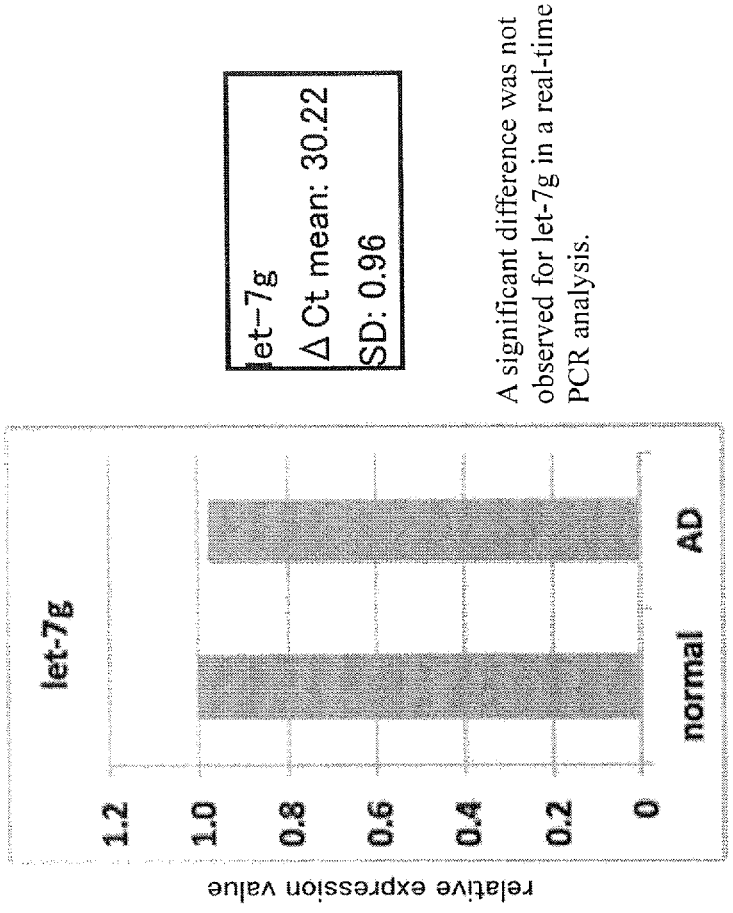
FIG. 10 is a diagram showing the comparison of relative expression values of let-7g between healthy individuals and Alzheimer's disease patients obtained in the example below.

Measurement of let-7g was performed on the healthy individuals and the Alzheimer's disease patients. The result is shown in FIG. 10. It was found that let-7g showed less variation so that it was successfully used as an internal control and advantageously succeeded in increasing the accuracy of diagnosis. Additionally, the base sequence of let-7g is as follows: ugagguaguaguuuguacaguu (SEQ ID NO: 6).

ΔCt values were normalized by using let-7g as an internal control. The measurement results of miR-122, let-7f and miR-144 are shown in FIGS. 11-A and 11-B.

Subsection 8. The Combination of MiR-122 and MiR-128-3p

Similarly to Subsection 5, ΔCt(miR-128)−(miR-122) was calculated in the 42 MCI patients. The result is shown in FIG. 12.

Figure 12:
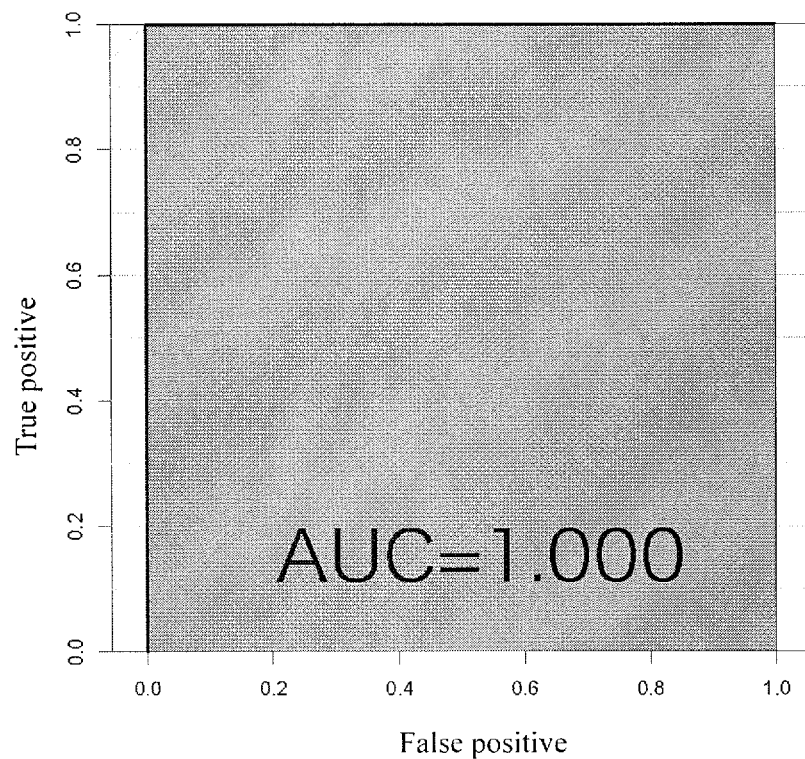
FIG. 12 is a diagram showing the AUC for the value of the formula $\Delta Ct^{(miR-128)} - \Delta Ct^{(miR-122)}$ obtained in the example below.

As shown in FIG. 12, the combination of miR-122 and miR-128-3p provided a surprising result as indicated by an AUC of 1.00 (i.e., a false positive rate of 0% and a false negative rate of 0%).

The invention claimed is:

1. A method of detecting and treating Alzheimer's disease or mild cognitive impairment in a subject, the method comprising the step of:
   measuring an amount of each of miR-122 and miR-128-3p present in plasma collected from the subject;
   comparing the measured amount of each of miR-122 and miR-128-3p in the subject with an amount of each of miR-122 and miR-128-3p in a healthy individual; and
   administering a medicine to slow down the progression of the Alzheimer's disease or mild cognitive impairment to the subject whose amount of miR-122 in the plasma is larger than that in the healthy individual and whose amount of miR-128-3p in the plasma is smaller than that in the healthy individual.

2. The method according to claim 1, wherein said measuring is performed by quantitative real-time PCR or a next generation sequencer.

3. The method according to claim 1, wherein an amount of let-7g-5p present in the plasma is also measured, and the measured amount of let-7g-5p is used as an internal control to normalize the measured amount of each of miR-122 and miR-128-3p.

* * * * *

SEQUENCE LISTING

<160> NUMBER OF SEQ ID NOS: 6

<210> SEQ ID NO 1

```
<211> LENGTH: 22
<212> TYPE: RNA
<213> ORGANISM: Homo sapiens

<400> SEQUENCE: 1
uggaguguga caauguguuu ug                                              22

<210> SEQ ID NO 2
<211> LENGTH: 22
<212> TYPE: RNA
<213> ORGANISM: Homo sapiens

<400> SEQUENCE: 2
ggauaucauc auauacugua ag                                              22

<210> SEQ ID NO 3
<211> LENGTH: 22
<212> TYPE: RNA
<213> ORGANISM: Homo sapiens

<400> SEQUENCE: 3
ugagguagua gauuguauag uu                                              22

<210> SEQ ID NO 4
<211> LENGTH: 21
<212> TYPE: RNA
<213> ORGANISM: Homo sapiens

<400> SEQUENCE: 4
ucacagugaa ccgguculcuu u                                              21

<210> SEQ ID NO 5
<211> LENGTH: 23
<212> TYPE: RNA
<213> ORGANISM: Homo sapiens

<400> SEQUENCE: 5
agcagcauug uacagggcua uca                                             23

<210> SEQ ID NO 6
<211> LENGTH: 22
<212> TYPE: RNA
<213> ORGANISM: Homo sapiens

<400> SEQUENCE: 6
ugagguagua guuuguacag uu                                              22
```